US009280147B2

(12) United States Patent
Riek

(10) Patent No.: US 9,280,147 B2
(45) Date of Patent: Mar. 8, 2016

(54) SYSTEM AND METHOD FOR ROBOTIC PATIENT SYNTHESIS

(71) Applicant: The University of Notre Dame du Lac, Notre Dame, IN (US)

(72) Inventor: Laurel Dawn Riek, Notre Dame, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/336,897

(22) Filed: Jul. 21, 2014

(65) Prior Publication Data

US 2015/0025681 A1   Jan. 22, 2015

Related U.S. Application Data

(60) Provisional application No. 61/856,380, filed on Jul. 19, 2013.

(51) Int. Cl.
*B25J 19/02* (2006.01)
*G05B 15/02* (2006.01)

(52) U.S. Cl.
CPC ..................................... *G05B 15/02* (2013.01)

(58) Field of Classification Search
CPC ........ A63H 11/00; B25J 13/00; B25J 13/081; B25J 9/1671; G06N 5/02
USPC ............. 700/245, 253, 258; 521/79; 434/267, 434/268, 262; 446/369-374, 385
See application file for complete search history.

(56) References Cited

U.S. PATENT DOCUMENTS

| | | | | |
|---|---|---|---|---|
| 7,113,848 | B2 * | 9/2006 | Hanson | 700/245 |
| 7,844,467 | B1 * | 11/2010 | Cosatto et al. | 704/275 |
| 8,311,791 | B1 * | 11/2012 | Avisar | 703/11 |
| 2004/0210345 | A1 | 10/2004 | Noda et al. | |
| 2007/0038331 | A1 | 2/2007 | Hanson | |
| 2009/0319459 | A1 | 12/2009 | Breazeal et al. | |
| 2013/0078600 | A1 | 3/2013 | Fischer et al. | |

OTHER PUBLICATIONS

International Search Report and Written Opinion for PCT/US2014/051334, dated Dec. 3, 2014, 10 pages.

* cited by examiner

*Primary Examiner* — Dalena Tran
(74) *Attorney, Agent, or Firm* — Greenberg Traurig, LLP

(57) ABSTRACT

Some embodiments of the invention include a robotic patient system including a computer system including a processor and a coupled sensor, and a control system configured to receive control data. The robotic patient system also includes a synthetic patient robot including a feature detector and action selector configured to actuate the robot based at least in part on the control data. Some further embodiments of the invention include a computer-implemented method of providing a robotic synthetic patient by providing a synthetic patient robot, configuring a control system to receive control data, extracting and converting a feature from the control data, and converting to an actuator command to move the robotic patient system. Some embodiments include a robot including a computer system including a processor, a non-transitory computer-readable storage medium, and a control system configured to be coupled to a source of control data to control the robot substantially autonomously.

35 Claims, 10 Drawing Sheets

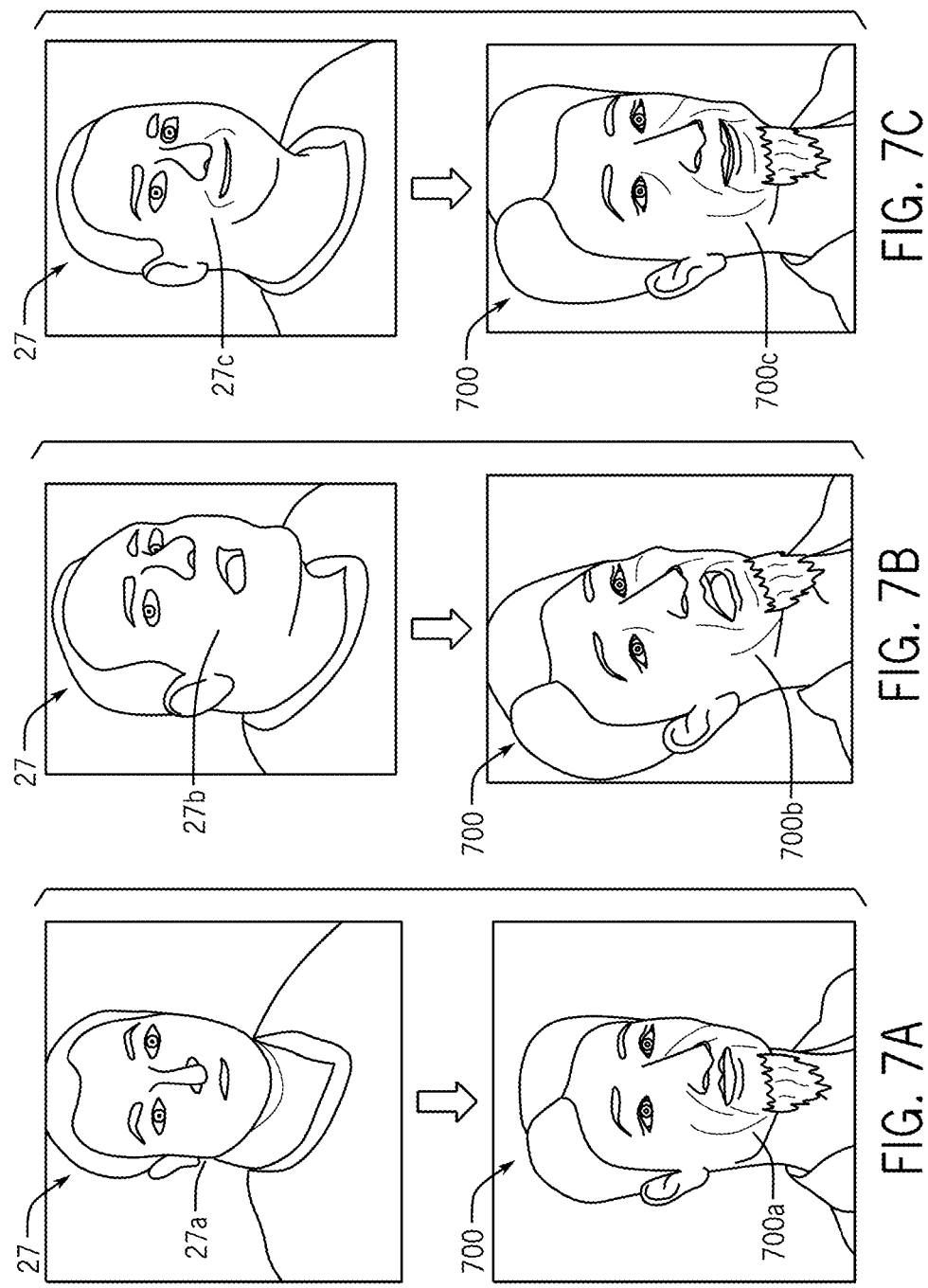

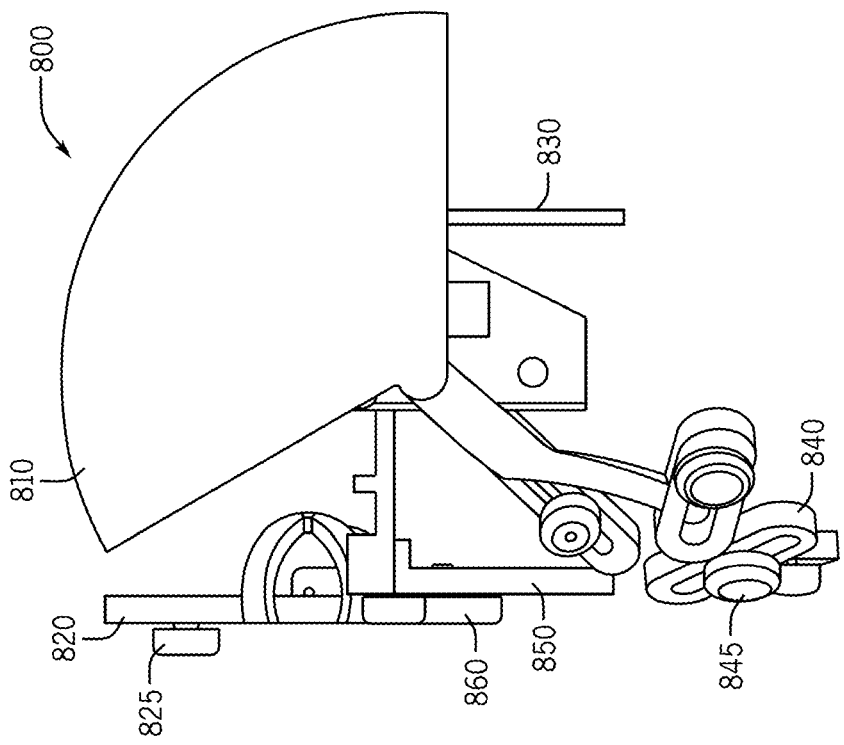
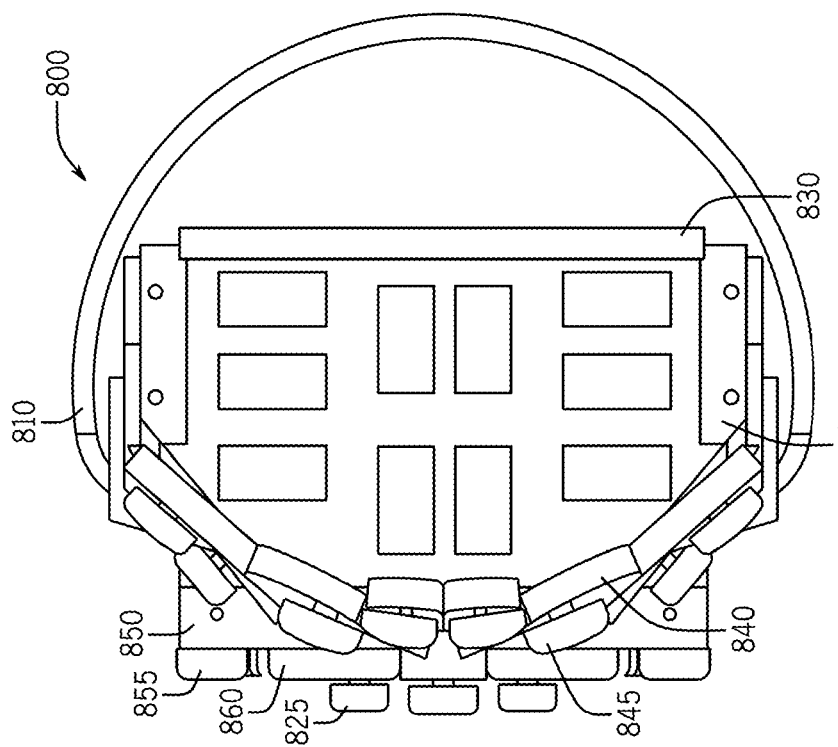
FIG. 9B
FIG. 9A

SYSTEM AND METHOD FOR ROBOTIC PATIENT SYNTHESIS

CROSS REFERENCE TO RELATED APPLICATIONS

This application claims the benefit of filing date of U.S. Provisional Application Ser. No. 61/856,380 titled "EXPRESSIVE ROBOTS FOR IMPROVING MEDICAL EDUCATION" filed on the Jul. 19, 2013, the specification of which is incorporated by reference herein in its entirety.

STATEMENT REGARDING FEDERAL SPONSORED RESEARCH OR DEVELOPMENT

Some research conducted for conception and development of at least one embodiment of the invention described herein was made using Federal awarded by the National Science Foundation under Grant No. IIS-1253935. The U.S. Federal Government has certain rights in the invention.

BACKGROUND

In the United States, there are an estimated 98,000 people killed each year and $17.1 billion dollars lost due to medical errors. One way to prevent these errors is through the use of simulation-based education on human patient simulator systems ("HPS"). HPS systems are perhaps the most commonly used android robots in the United States, and domestically comprise a $70 million dollar industry. Simulated patients provide safe experiences for clinical trainees, where they can practice communication, assessment, and intervention skills, without fear of harming a real patient. Although this technology is in widespread use today, commercial patient simulators lack sufficient realism. Despite the vital importance of non-verbal expressivity to providing cues to clinicians for how to assess and treat patients, currently available commercial HPS systems include static faces and mouth positions, and generally immobile, non-animated body portions, with no capability to convey facial expressions, gaze, and realistic mouth movements, etc. In particular, these simulators cannot convey visual signals of pain to medical trainees, even though perceiving a patient's nonverbal pain cues is an exceptionally important factor in how clinicians make decisions. As a result, existing systems may be preventing students from picking up on patients' pain signals, possibly inculcating poor safety habits due to a lack of realism in the simulation.

SUMMARY

Some embodiments of the invention include a robotic patient system comprising a computer system including at least one processor, at least one coupled sensor, and a control system coupled to at least one source of control data. The control system comprises a command interface, a feature detector and action selector, and a server coupled to the command interface. Further, the robotic patient system comprises a synthetic patient robot comprising a robotic head assembly and at least one actuator. The feature detector and action selector are configured to be coupled to the command interface using a link, and at least a portion of the synthetic patient robot is configured to respond to the control data.

In some embodiments, the control system further comprises a feature tracker and the server is coupled to the feature tracker and the feature detector and action selector. In some embodiments, the at least one actuator is configured to receive commands from the command interface via the feature detector and action selector under control of the server.

In some embodiments of the invention, the control data comprises pre-recorded data. In some embodiments, the control data comprises substantially real time collected information, and the synthetic robot responds at least in part based on the control data substantially in real time.

In some embodiments, the control data is derived from a patient image, an actor, an operator, or a patient medical record. In some embodiments of the invention, at least a portion of the control data is derived from the at least one sensor. In some further embodiments, the at least one sensor comprises a camera and at least a portion of the control data is derived from at least one image. Some embodiments of the invention include a robotic patient system where at least a portion of the control data is received from an operator.

Some embodiments of the invention comprise a synthetic patient robot that comprises a wireless interface, and the link comprises the wireless interface wirelessly coupled to the control system. In some other embodiments, the link comprises a wired interface.

In some embodiments, the robotic head assembly includes at least one slider configured to be actuated by the at least one actuator. In some embodiments of the invention, actuation of the at least one slider is not audible outside of the synthetic patient robot. In some further embodiments, the robotic head assembly comprises an outer skin where at least a portion of the outer skin can be moved by the at least one actuator. In some embodiments, movement of at least a portion of the outer skin induces or changes a perceived expression from the synthetic patient robot. Further, in some embodiments, the outer skin is interchangeable and configurable to modify a perception of at least one of race, ethnicity, age, or gender.

In some embodiments, the synthetic patient robot includes a sound generator. Further, some embodiments include a sound generator that is configured to emit sound based at least in part on the control data or the at least one actuator. In some embodiments, the at least one actuator comprises at least one sensor responsive to external stimuli. In some further embodiments, at least a portion of the robotic head assembly can be actuated to provide a perceivable expression, and can be configured to substantially simultaneously emit sound following a detected response from external stimuli.

Some embodiments of the invention comprise a computer-implemented method of providing a robotic synthetic patient comprising providing a computer system including at least one processor and at least one coupled sensor, receiving control data from at least one control data source. Further, the computer-implemented method includes providing a control system comprising a command interface, a feature detector and action selector, and a server coupled to the command interface. The computer-implemented method also comprises providing a synthetic patient robot comprising the feature detector and action selector and a robotic head assembly and at least one actuator. The computer-implemented method also comprises using the at least one processor, and configuring the control system to receive the control data. The computer-implemented method also comprises using the at least one processor to extract and convert at least one feature from the control data to at least one actuator command, where at least a portion of the synthetic patient robot is configured to respond to the to the at least one actuator command.

In some embodiments of the computer-implemented method the control system further comprises a feature tracker and a feature detector and action selector, and the server is coupled to the feature tracker and the feature detector and action selector. In this instance, the at least one feature is processed by the feature tracker and the feature detector and action selector to produce the least one actuator command.

In some embodiments of the computer-implemented method, the control data comprises information derived from at least one patient image. In some embodiments, the at least one patient image is pre-recorded. In some further embodiments, the control data comprises substantially real time collected information, and when the control data is received, the synthetic robot responds to the least one actuator command at least in part based on the control data substantially in real time.

In some embodiments, the at least one actuator command can be modified based at least in part on input from an operator. In some embodiments, the control data is derived from at least a partial portion of the face of the operator. In some embodiments, the control data is received from the operator. In some further embodiments, the control data is received from the synthetic patient robot. Some embodiments include a synthetic patient robot that is configured to operate substantially autonomously.

Some embodiments of the invention include a synthetic patient robot comprising a computer system including at least one processor, a non-transitory computer-readable storage medium in data communication with the processor, and a control system configured to be coupled to at least one source of control data. The synthetic patient robot also comprises a robotic head assembly and at least one actuator, where at least a portion of the synthetic patient robot is configured to be operated substantially autonomously by the control system based at least in part on the control data.

In some embodiments of the robot, the at least one source of control data is the non-transitory computer-readable storage medium. In some embodiments, the control data is received by the synthetic patient robot prior to operation of the synthetic patient robot. In some further embodiments, the control data is received by the synthetic patient robot substantially in real time during operation of the synthetic patient robot. In some other embodiments, the control data comprises information derived from at least one of a patient image, an actor, an operator, or a patient medical record.

DESCRIPTION OF THE DRAWINGS

FIG. 7A illustrates transfer of a patient expression to an expressive robot with patient expression synthesis in accordance with some embodiments of the invention.

FIG. 7B illustrates transfer of a patient expression to an expressive robot with patient expression synthesis in accordance with another embodiment of the invention.

FIG. 7C illustrates transfer of a patient expression to an expressive robot with patient expression synthesis in accordance with further embodiments of the invention.

FIG. 9A shows a bottom view of a robot head assembly in accordance with some embodiments of the invention.

FIG. 9B shows a side view of a robot head assembly in accordance with some embodiments of the invention.

DETAILED DESCRIPTION

Figure 1:
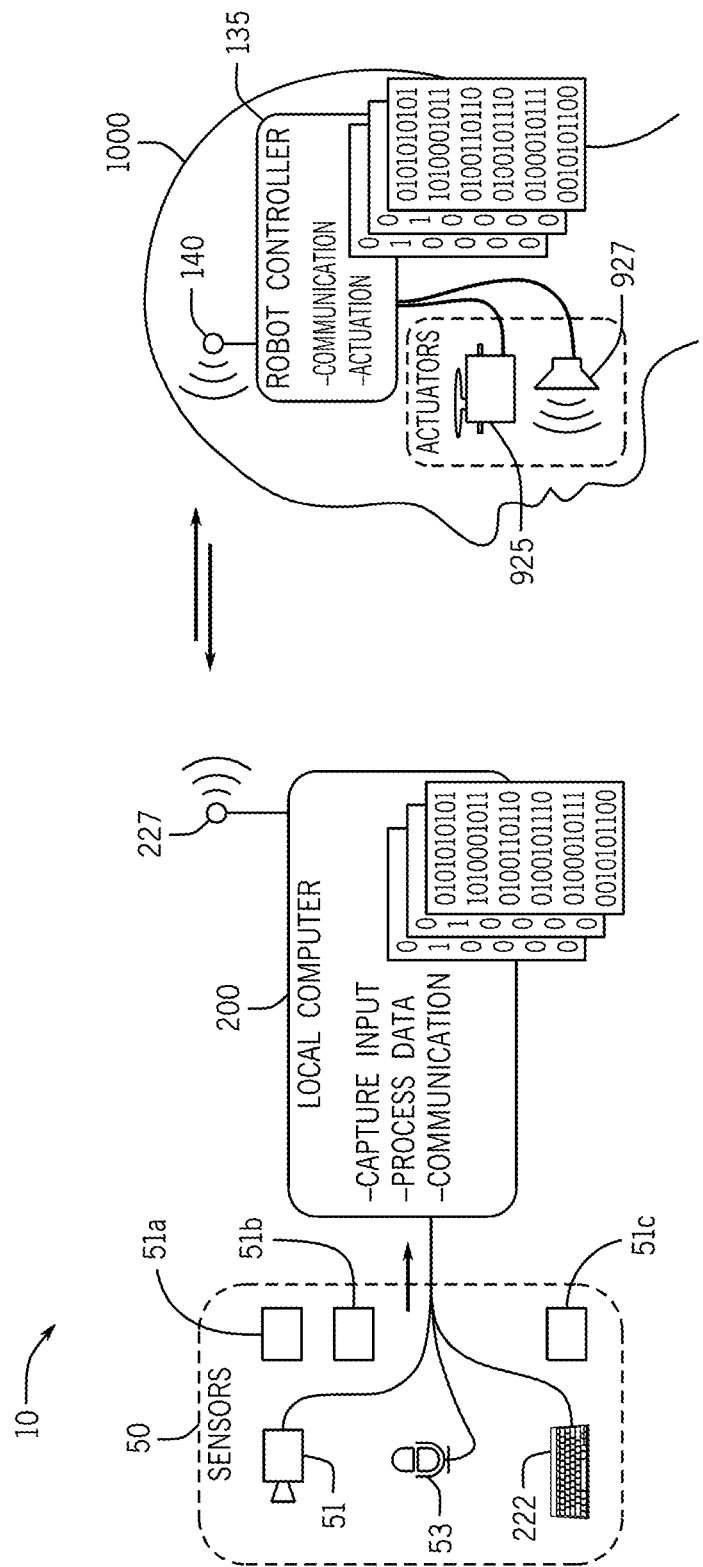
FIG. 1 illustrates a synthetic patient system and method in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Some of embodiments of the invention as described herein generally relate to patient simulator systems, and methods to control patient simulators by enabling them to convey realistic, patient-driven facial expressions to clinical trainees. Some embodiments of the invention include a robotic physical patient simulator and associated control systems that provide a wider range of expressivity, including the ability to express pain and other pathologies in its face. Further, in some embodiments, an operator can directly puppeteer a robotic patient face during a simulation, pretending to be the patient.

For example, FIG. 1 illustrates a synthetic patient system and method 10 in accordance with some embodiments of the invention. In some embodiments, the system and methods of the synthetic patient system and method 10 can comprise at least one computing system 200 configured to perform various processes and methods to remotely control and actuate a synthetic patient system 1000. More specifically, the synthetic patient system and method 10 can comprise at least one computing system 200 configured to process a capture and/or process at least one video frame or image of a patient or simulated patient, process at least one feature or expression from the video frame or image, and generate at least one control sequence. In some embodiments, the at least one control sequence can remotely control and actuate a synthetic patient system 1000, based at least in part on at least one feature or expression from the patient or simulated patient. As used herein, a simulated patient can comprise an actor acting as a patient. For example, in some embodiments, the simulated patient can comprise a trainer or operator 25 acting as a patient. In some embodiments, the simulated patient can comprise a nurse, physician, a medical student, or other personnel working in the medical profession. In some other embodiments, the simulated patient can comprise an actor simulating a patient under instruction from another individual such as the trainer or operator 25, or other individual with knowledge of patients and patient symptoms.

Figure 2:
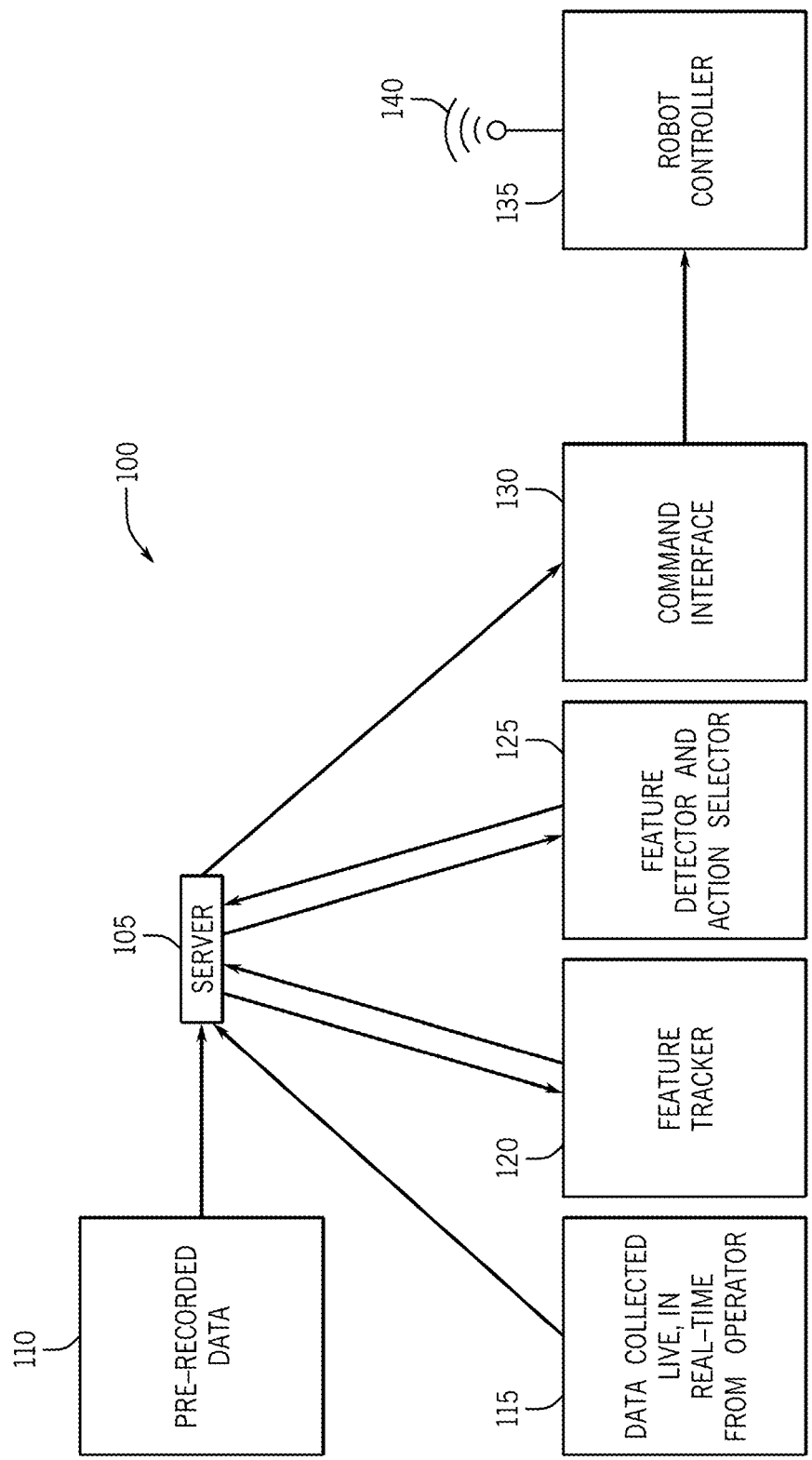
FIG. 2 illustrates a control system for the synthetic patient system and methods of FIG. 1 in accordance with some embodiments of the invention.

FIG. 2 illustrates a control system 100 that can be used for the synthetic patient system and method 10 of FIG. 1 in accordance with some embodiments of the invention. Further, in some embodiments, various types of input devices 50, can allow the user to provide command or input to the computer system 200, or capture data for use substantially in real time and/or for later use. For example, in some embodiments, the computer system 200 can optionally include various sensors 50. In some embodiments, the computer system 200 can be coupled to at least one camera 51, and at least one sound recording and capture device 53 (e.g., such as a microphone). In some embodiments, the camera 51 can comprise a movie or video camera (e.g., such as a web-cam), a still image camera. In some further embodiments, the camera 51 can comprise an infra-red camera 51b, and/or any a conventional camera sensitive to red, green, and blue light, and/or a time-of-flight camera. In some further embodiments, the camera 51 can comprise any other conventional optical sensor. Further, the computer system 200 can also include other conventional peripheral devices such as speakers coupled to sound cards, and/or video cards coupled to the camera 51, and optionally other conventional video capture devices and cameras (such as for example cameras or video systems aimed at the synthetic patient system 1000 and/or its surroundings). In some embodiments, the camera 51 and/or the capture device 53 can be coupled to the computer system 200 using a wired or a wireless coupling. In some further embodiments, one or more of the sensors 50 can comprise an electrooculography sensor, an electronystagmography sensor, an electrocardiography sensor, an electroencephalography sensor, or an electromyography sensor.

In some embodiments, the control system 100 can include algorithms for automatic facial feature extraction, facial expression detection and synthesis of facial features and facial expressions. As depicted in FIG. 2, in some embodiments, the control system 100 can include data and information (i.e. control data 110) derived from a patient and/or simulated patient data and information. In some embodiments, the control data 110 can come from a patient, an actor, or an operator 25. Further, in some embodiments, the control data 110 can comprise a patient medical record.

For example, in some embodiments, the control data 110 can comprise video data comprising actual or simulated patient facial data. In some embodiments, the video data can comprise one or more continuous or discontinuous still-frame images that can be accessed by a server 105. In some embodiments, the control data 110 can comprise pre-recorded image data. In some embodiments, the synthetic patient system 1000 can blend expressivity (i.e., masking) between a live operator and pre-recorded data. In some other embodiments, the control system 100 can include data and information comprising control data 115 that comprises real-time image data. In some embodiments, the control data 110, 115 can comprise still image and/or video data from the at least one camera 51. In some embodiments, other information can be captured from a patient's face. For example, in some embodiments, marker-based motion capture or markerless based motion capture can be used to capture facial movements and expressions.

In some further embodiments, the control data 110, 115 can comprise audio data. For example, in some embodiments, audio from a patient can be recorded and used for the control data 110, 115. In other embodiments, the control data 110, 115 can comprise simulated patient audio data. In some embodiments, the control data 110, 115 comprising audio data can be used to animate the synthetic patient system 1000 to provide an impression of the synthetic patient system 1000 making a sound or creating speech.

In some further embodiments, the control data 110, 115 can comprise information other than still image, video, or audio data. For example, in some embodiments, the control data 110, 115 can comprise one or more descriptions of a medical condition (e.g., a description of a stroke and/or indication of facial paralysis). In some further embodiments, the control data 110, 115 can comprise one or more instructions that can be interpreted by the control system 100 and/or the synthetic patient system 1000 to control at least a portion of the synthetic patient system 1000. In some embodiments, the control data can comprise instructions to provide slurred speech, including a condition of aphasia, affecting language and intonation responses in the synthetic patient system 1000.

In some embodiments, the control data 110, 115 can be transferred and stored in the computer system 200 (e.g. in mass storage device 207), and accessed by the server 105. For example, in some embodiments, control data 110 can be recorded by the camera 51, stored temporarily in the computer system 200, and after some period of time, accessed by the server 105. In some other embodiments, the control data 110, 115 can comprise image data taken from a recording device not coupled to the computer system 200. For example, in some embodiments, the image data can be transferred from another source, including for example an external camera. In some embodiments, the control data 110, 115 can comprise image data taken from a database or other image data source.

In some further embodiments, the control system 100 can comprise real-time image data. For example, in some embodiments, the control system 100 can include the server 105 accessing real-time image data. In some embodiments, control data 115 comprising real-time image data can include live-action or real-time video (e.g., taken using a camera 51). In some further embodiments, the control data 115 comprising real-time image data can be accessed substantially in real-time using at least one sensor 50 (e.g. camera 51), and the still-frame and/or motion-video can be accessed directly by the server 105.

In some embodiments, the control system 100 can comprise a feature tracker 120 coupled to the server 105. In some embodiments, control data 110,115 can be processed to create a set of feature points that can be mapped to a controller of a virtual or physical manikin such as a synthetic patient system 1000. For example, in some embodiments, the control system 100 can comprise the robot controller 135 that can be configured to control one or more actuators within the synthetic patient system 1000. In some embodiments, the actuators can comprise servos or other conventional electromechanical devices capable of enabling movement of one or more components of the synthetic patient system 1000. For example, in some embodiments, the actuators can comprise servo motors, and/or linear or rotary drives. In some embodiments, the actuator can comprise an assembly combination of a motor, one or more gears, and one or more output shafts.

In some embodiments, the control system 100 can comprise a feature detector and action selector 125. In some embodiments, the feature detector and action selector 125 coupled to the server 105 can process feature points from the feature tracker 120. In some embodiments, the feature detector and action selector 125 can receive and process a mesh of feature points produced by the feature tracker 120 to determine and filter various actuator control commands. The feature detector can track any portion of a body including a face, abdomen, arms and legs, etc., and can include gestures, postures, or other signals. In some further embodiments, the control system 100 can comprise a command interface 130. Further, in some embodiments, the command interface 130 can be configured to communicate one or more actuator control commands to a robot controller 135. For example, in some embodiments, the control system 100, comprising the robot controller 135, can be coupled to the robot controller 135 using a wired or wireless link. In some embodiments, the computer system 200 can comprise a wireless link 227, and the control system 100 can comprise a transceiver 140. In some embodiments, the wireless link 227 can be configured to electromagnetically couple to the transceiver 140 to transfer data between the robot controller 135 and the command interface 130 portion of the control system 100 (via the server 105). Accordingly, in some embodiments, the feature detector and action selector 125 can process at least one actuator command that can be remotely communicated by the command interface 130 through the wireless link 227, and received and communicated to the robot controller 135 via the transceiver 140. Moreover, in some embodiments, the synthetic patient system 1000 can comprise the robot controller 135. In this instance, the at least one actuator command can be remotely communicated to synthetic patient system 1000 by remotely communicating from the command interface 130 through the wireless link 227 of the computer system 200, where the at least one actuator command can be received and communicated to the robot controller 135 via the transceiver 140.

In some further embodiments, the synthetic patient system 1000 can be fully or partially autonomous. In other words, in some embodiments, the synthetic patient system 1000 can operate independently or partially independently from an operator 25. For example, in some embodiments of the invention, some or all of the control system 100 can be integrated within the synthetic patient system 1000, and configured to enable the synthetic patient system 1000 to operate with little or no direct input and/or feedback from an operator 25. Moreover, in some embodiments, the synthetic patient system 1000 can include an adjustable autonomy, where the operator can switch between various modes or degrees of autonomy.

In some embodiments of the invention, control data 110 (pre-recorded image data) can be transferred to the synthetic patient system 1000 (e.g. via the transceiver 140). In some other embodiments, control data 110 can be stored within the synthetic patient system 1000. For example, in some embodiments, control data 110 can be transferred to the synthetic patient system 1000 and stored within the synthetic patient system 1000. In some further embodiments, the control data 110 can be transferred to the synthetic patient system 1000 when the synthetic patient system 1000 is assembled. In some other embodiments, the synthetic patient system 1000 can be configured to operate without the control system 100. For example, in some embodiments, the synthetic patient system 1000 can include conventional control systems capable of operating the synthetic patient system 1000.

Figure 3:
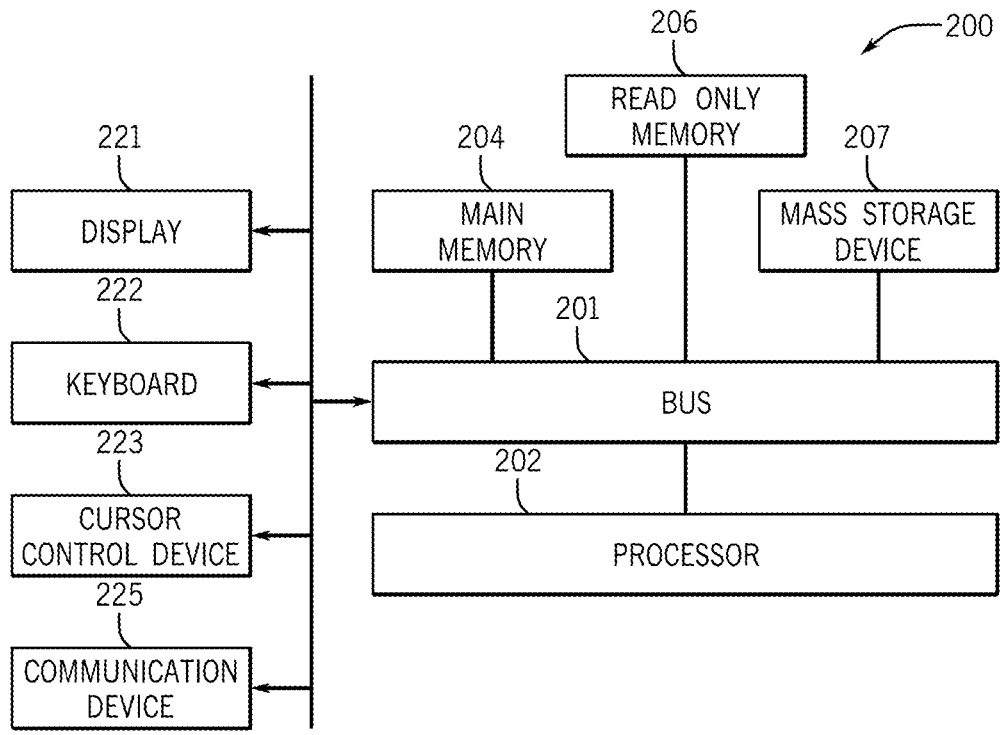
FIG. 3 is a block diagram of a computer system that can be used within the control system of FIG. 2 for implementing the synthetic patient system and methods of FIG. 1 configured in accordance with some embodiments of the invention.

The various components and interoperability of the computer system 200 can be further illustrated in FIG. 3, in which the features of some embodiments of the invention can be implemented. In some embodiments, the computer system 200 can include a bus 201 for communicating information between the components in the computer system 200. Further, in some embodiments, at least one processor 202 can be coupled with the bus 201 for executing software code, or instructions, and processing information (including information related to information regarding persons having online profiles on dating websites). In some embodiments, the computer system 200 further compromises a main memory 204, which can be implemented using random access memory (RAM) and/or other random memory storage devices. In some embodiments, the main memory 204 can be coupled to the bus 201 for storing information and instructions to be executed by the processor 202. Further, in some embodiments, the main memory 204 also can be used for storing temporary variables or other intermediate information during the execution of instructions by the processor 202. In some embodiments, the computer system 200 can also include a read only (ROM) and/or other static storage device coupled to the bus 201 for storing static information and instructions for the processor 202.

In some embodiments of the invention, the computer system 200 can include one or more peripheral components enabling user interaction with the system 200. For example, in some embodiments, the system 200 can include a cursor control device 223, such as a conventional mouse, touch mouse, trackball, track pad, or other type of cursor direction keys for communicating direction information and command selection to the processor 202 and for controlling movement of a cursor on the display 221. Further, the system 200 can also include at least one keyboard 222 for data input, and facilitation of command and control of the various aspects of the system 200, and at least one communication device 225 operatively coupled to the processor 202 via the bus 201.

In some embodiments, the system 200 can include wearable components. For example, in some embodiments, some portions of or all of the system 200 can be implemented within a wearable computer platform. In some embodiments, some portions of or all of the system 200 can be mounted on the operator 25, and can be configured to enable the operator to operate and control at least a portion of the synthetic patient system 1000.

In some further embodiments, the system 200 can include at least one gesture interface. For example, in some embodiments, an optical, infra-red or RF transceiver can be used for gesture detection by an operator 25. In some embodiments, the computer system 200 can optionally include various sensors 50 that comprise a gesture detector 51*a*. In some embodiments for example, gesture information can be measured by a Microsoft Kinect™ system ("Kinect" is a registered trademark of Microsoft Corporation).

In some embodiments of the invention, the computer system 200 can implement the system and method shown in FIG. 1 using the control system 100 shown in FIG. 2 using one or more processors residing in one or more conventional computer platforms. In some embodiments, the computer system 200 can include a network interface and an application interface coupled to at least one processor 202 capable of running at least one operating system. Further, in some embodiments, the computer system 200 can include a network interface and an application interface coupled to at least one processor 202 capable of running one or more of the software modules (e.g., enterprise applications). In some embodiments, the software modules can include a software platform that can include numerous other software modules suitable for hosting at least one account and at least one user account, as well as transferring data between one or more accounts.

Figure 4:
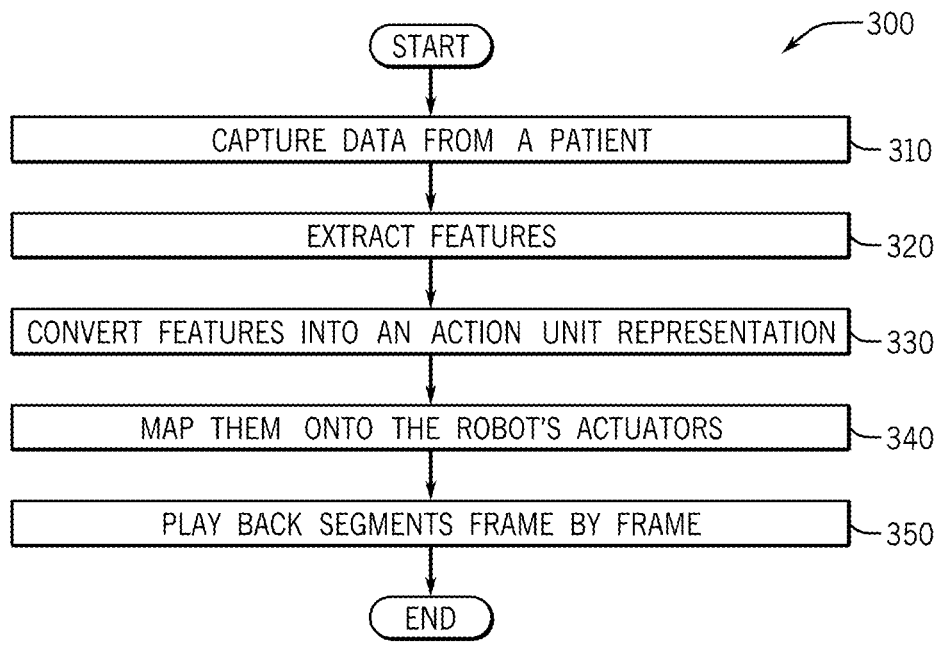
FIG. 4 illustrates an operational sequence flowchart for the synthetic patient system and methods of FIG. 1 in accordance with some embodiments of the invention.

In some embodiments, the computer system 200, using the control system 100, can provide for facial feature extraction, facial expression detection and synthesis of facial features and facial expressions. In some embodiments, methods for imaging, facial feature detection and extraction, and synthesis of facial features using the synthetic patient system 1000 can be described by FIG. 4 which illustrates an operational sequence flowchart 300 for the synthetic patient system and methods of FIG. 1 in accordance with some embodiments of the invention. In some embodiments, the operational sequence flowchart 300 can comprise a series of process steps including process step 310. As described above with respect to the control system 100 of FIG. 2, in some embodiments, actual patient and/or simulated patient data can be used for the control data 110, 115, including for example video data comprising a series of still-frame images of a patient's face.

In some further embodiments, step 320 includes extracting one or more features from the patient's face (i.e., taken from at least one frame of the video taken in step 310). For example in some embodiments, some portion of the control data 110, 115 can be processed by the control system 100 to create a set of feature data that can be used to control the synthetic patient system 1000. In some embodiments, the feature tracker 120 can comprise a constrained local model (hereafter termed "CLM") based tracker. In some embodiments, the feature tracker 120 can use the CLM to extract a series of feature points frame-by-frame from the control data 110, 115.

In some embodiments of the invention, the source videos (control data 110, 115) can include patient images depicting various emotional and/or physiological responses and expressions. For example, in some embodiments the source videos can comprises videos of patients expressing some level of pain or discomfort. In some embodiments, the source videos can be extracted from the UNBC— McMaster Pain Archive (P. Lucey, J. F. Cohn, K. M. Prkachin, P. E. Solomon, and I. Matthews, "Painful data: The UNBC-McMaster shoulder pain expression archive database," in IEEE International Conference on Automatic Face & Gesture Recognition, 2011". In some further embodiments, the source videos can comprise individuals expressing other naturalistic expressions, such as from the Belfast Naturalistic Emotional Database (Douglas-Cowie, E., Cowie, R., Sneddon, I., Cox, C., Lowry, O., Mcrorie, M., . . . & Karpouzis, K. (2007). The HUMANE database: addressing the collection and annotation of naturalistic and induced emotional data (in *Affective computing and intelligent interaction* (pp. 488-500). Springer Berlin Heidelberg.). In some further embodiments, the source videos can comprise patients with one or more medical conditions including, but not limited to stroke, dystonia, cerebral palsy, Moebius syndrome, and Parkinson's disease.

Referring again to FIGS. 2 and 4, in some embodiments, in step 330, the feature tracker 120 coupled to the server 105 can create action unit representations based on the control data 110, 115 by converting the features extracted in step 320. In some embodiments, the aforementioned CLM-based tracker can extract the feature points frame-by-frame from each source video (derived from the control data 110, 115), and these feature points can then be mapped to control actuator motors of a virtual or synthetic patient. For example, in step 340, actuator control command created produced by the feature detector and action selector 125 of the control system 100 can be processed to create a set of action unit represented feature points that can be mapped to the robot controller 135 of a synthetic patient system 1000, and in step 350, segments can be played back frame by frame, and any one of the processes shown in steps 310, 320, 330, 340, 350 can be repeated. Further, in some embodiments, step 330 can be skipped, and translation can occur through steps 320, 340.

In some embodiments of the invention, a trainer or operator 25 can use the control system 100 within the synthetic patient system and method 10 to provide substantially real-time command and control of a synthetic patient system 1000 using one or more control sequences based at least in part on at least one feature of a simulated patient expression. In some embodiments, this can be illustrated in FIG. 5, which shows an operational sequence flowchart 400 for the synthetic patient system and methods of FIG. 1. In some embodiments, step 410 can include an input of a video frame. In some embodiments, operator 25 (in this example shown seated in front of the computer system 200) can enable or instruct the control system 100 to provide control data 110, 115. In some embodiments, the control data 110, 115 can comprise a video sequence captured using the sensor 50. Further, in some instances as depicted, the operator 25 can provide an acted image and the sensor 50 (e.g., comprising a camera 51) can collect real time control data 115 of the operator 25 acting as a patient. For example, in some embodiments, the operator 25 can provide at least one facial expression, and the camera 51 can capture real time control data 115 capturing one or more of the facial expressions. Any facial expression can be captured as the control data 115. For example, facial expression indicative of pain, anger, or disgust, surprise, or any other human emotion can be captured by the camera 51. Further, non-emotional actions including blinking, squinting, yawning, etc., can be captured and translated.

In some further embodiments, a trainer or operator 25 can provide substantially real-time command and control of the synthetic patient system 1000 without the use of control data 110, 115. For example, in some embodiments, one or more portions of the synthetic patient system 1000 can be controlled directly by the operator 25 without additional control from the control system 100 based on control data 110, 115 without using patient data such as control data 110, 115. Moreover, in some embodiments, a trainer or operator 25 can provide substantially real-time command and control of the synthetic patient system 1000 without or in addition to acting as a patient. For example, in some embodiments, the trainer or operator 25 can control various aspects of the synthetic patient system 1000 (including moving portions of the synthetic patient system 1000 and/or instructing the synthetic patient system 1000 to emit sounds) without acting as a patient, or while acting as a patient (thereby providing control data 110).

In some other embodiments of the invention, one or more portions of the synthetic patient system 1000 can be controlled based at least in part on data from one or more sensors within the synthetic patient system 1000. For example, in some embodiments, the synthetic patient system 1000 can include at least one integrated touch, impact and/or pain sensor (e.g., simulated nerve and/or pain receptors sensors embedded can be embedded within the outer skin 950 of the synthetic patient system 1000 shown in FIG. 13, or any portion of the system 1000 including patient abdomen 1001). In some embodiments, the sensor can be coupled to the control system 100. In some further embodiments, one or more integrated touch, impact and/or pain sensors can operate independently (or partially independently) of the control system 100. For example, if the synthetic patient system 1000 is pricked by a needle, one or more integrated touch, impact and/or pain sensors can send a signal and/or be sensed by the control system 100. In this instance, sensing and/or actuation of the at least one integrated touch, impact and/or pain sensor can cause the synthetic patient system 1000 to emit an audible sound (e.g., an "ouch" sound) and/or to move a portion of the synthetic patient system 1000 (e.g., such as to move a portion of the outer skin 950 and/or any other portion of the system 1000 including any portion of the robot assemblies 800, 900 shown in FIGS. 8A-9B, and 10). Further, portions of the synthetic patient system 1000 can respond (independently or in response to the external stimuli). For example, the eyes can widen, and/or the eyebrows can raise, and/or the facial expression can change, and some portion of the system 1000 including patient abdomen 1001 can quickly move, and/or twitch, etc.

Referring back to FIG. 5, following video frame capture in step 410, in some embodiments, the process 400 can proceed with feature extraction processes. As described earlier, in some embodiments, the feature tracker 120 can use a CLM-based tracker to extract a series of feature points frame-by-frame (in this example, from control data 115). CLM is a shape-based tracking technique similar to "Active Appearance models" ("AAM"). AAMs are statistical methods for matching the model of a user's face to an unseen face. A CLM-based approach is similar to an AAM-based approach, except it is person-independent, and does not require any manual labeling of an actor's face. Some features of the CLM-based approach can be found in the following references, each of which is incorporated by reference in its entirety: T. Baltrusaitis, P. Robinson, and L. Morency, "3d constrained local model for rigid and non-rigid facial tracking," in CVPR, 2012, S. W. Chew, P. Lucey, S. Lucey, J. Saragih, J. F. Cohn, and S. Sridharan, "Person-independent facial expression detection using constrained local models," in IEEE Int'l Conf. on Automatic Face and Gesture Recognition (FG), 2011, and D. Cristinacce and T. Cootes, "Feature detection and tracking with constrained local models," in Proceedings of British Machine Vision Conference, vol. 3, 2006.

Cristiannace and Cootes (described in Cristinacce, D. and Cootes, T. 2008. "Automatic feature localisation with constrained local models. Pattern recognition", 41, 10 (October 2008), 3054-3067, and incorporated herein by reference), and Saragih et al. (described in Saragih, J. M., Lucey, S. and Cohn, J. F. 2010. "Deformable Model Fitting by Regularized Landmark Mean-Shift. International Journal of Computer Vision", 91, 2 (September 2010), 200-215, and incorporated herein by reference), provide a detailed description of the CLM algorithm, but it is described briefly below. The shape model of a 3D CLM is defined by a 3D mesh and in particular the 3D vertex locations of the mesh. A shape, s, is the coordinates of n vertices that comprise the mesh:

$$s = [x_1, y_1, z_1, \ldots, x_n, y_n, z_n]$$

The shape is aligned based on vertex locations that correspond to the source image. The shape can be expressed as a base shape, $S_0$, plus a linear combinations of m shape vectors $S_i \in R^{3N}$ (i=1, ... m).

$$s = s_0 + \sum_{i=1}^{m} p_i s_i$$

where the coefficients $p=(p_1, \ldots, p_m)^T$ are the shape parameters. These can be further divided into rigid parameters $p_s$ (e.g., head pose), and non-rigid parameters $p_0$ (e.g., expressions), such that $p^T=[p^T s, p^T o]$ For a 3D CLM, the model is fitted to an unseen image iteratively, by using the current parameter estimates to generate templates, correlating the target image with the templates to generate response images, and then optimizing the shape parameters to maximize the sum of responses. Then, Procrustes alignment (described in Cootes, T. F., Edwards, G. J. and Taylor, C. J. 2001, "Active appearance models", IEEE Transactions on Pattern Analysis and Machine Intelligence. 23, 6 (2001), 681-685, and incorporated herein by reference) can be used to estimate the base shape of $S_0$, and a number of algorithms are used to calculate s, such as linear SVMs (described in Jeni, L. A., Takacs, D. and Lorincz, A. 2011., "High Quality Facial Expression Recognition in Video Streams using Shape Related Information only", 2011 IEEE International Conference on Computer Vision Workshops, 2168-2174, and incorporated herein by reference), and PCA (described in Boker, S. M., Cohn, J. F., Theobald, B. J., Matthews, I., Brick, T. R. and Spies, J. R. 2009, "Effects of damping head movement and facial expression in dyadic conversation using real-time facial expression tracking and synthesized avatars", Philosophical Transactions of the Royal Society B: Biological Sciences. 364, 1535, December 2009, 3485-3495, and incorporated herein by reference).

Figure 6A:
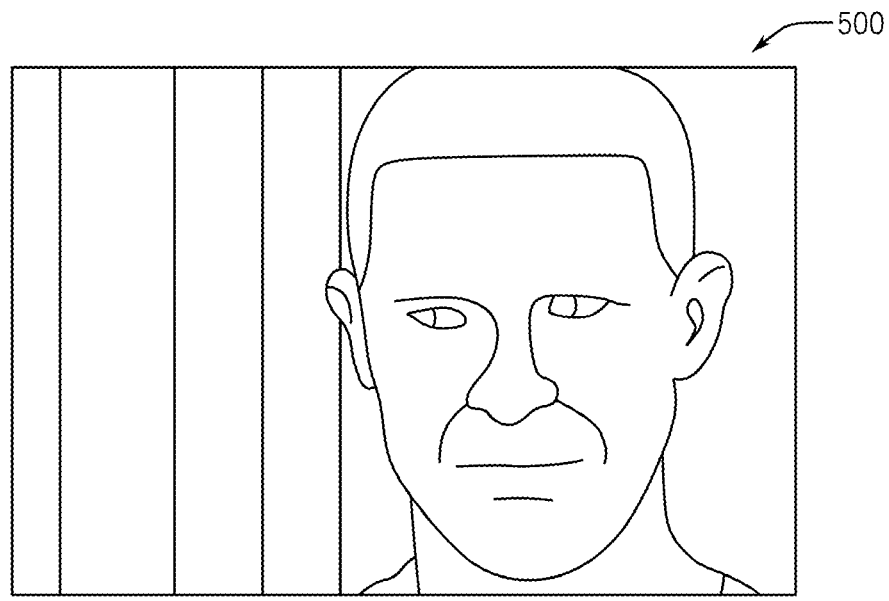
FIG. 6A depicts one frame of a patient video in accordance with some embodiments of the invention.
Figure 6B:
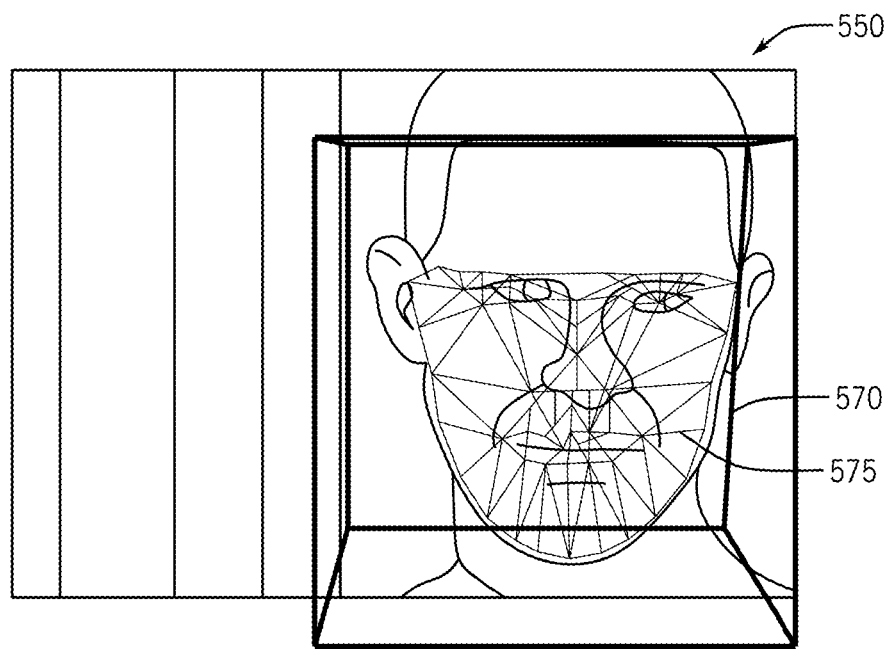
FIG. 6B depicts one frame of a patient video including markerless facial tracking in accordance with some embodiments of the invention.

In a CLM-based method, the shape of the face can be estimated by labeling some feature points on several facial images in the training set. For example, FIG. 6A depicts one frame 500 of a patient video (control data 110, 115), and FIG. 6B depicts one frame 550 of a patient video including markerless facial tracking. The frame 550 comprises the frame 500 with additions of a feature mesh 570 comprising mesh triangles bounded by one or more feature points 575. In some embodiments, the feature detector and action selector 125 coupled to the server 105 can process feature points 575 from the feature tracker 120. In some embodiments, in step 420, the feature detector and action selector 125 can receive and process a mesh of feature points 575 produced by the feature tracker 120 to determine and filter various actuator control commands. In some embodiments, the feature detector and action selector 125 receives the mesh data 570 and processes the coordinates of the mesh triangles. In some embodiments, the feature tracker 120 translates the tracked feature points 575 to actuator movements (which are sent to the server 105). For example, in some embodiments, the server 105 can communicate at least one actuator command 450 to the command interface 130, which can then be communicated to the robot controller 135 (e.g., via the transceiver 140 as described earlier).

In some embodiments, depth information can be provided by at least one sensor 50. For example, in some embodiments an optical, infra-red or RF transceiver can be used to determine depth. In some embodiments for example, depth information can be provided by a Microsoft Kinect™ system using sensor 51a. In some embodiments, the sensor 50 capable of depth detection can be used to detect the physical position of an operator 25, detect facial features and track distance. In some embodiments, this method is robust to light variations and head-pose rotations, and is thus an improvement over the traditional CLM method.

In some embodiments of the invention, at the frame level, each frame of the control data 110, 115 can be coded using a facial action coding scheme ("FACS"). In some embodiments, each frame can also receive, contain, or be assigned a pain score (e.g., ranging from 0 to 12). In some embodiments, this information can be associated with or tagged to one or more actuator control commands and/or other information sent to the synthetic patient system 1000. For example, in some embodiments, a pain score or other emotional or physiological response related variable can be associated with or tagged to one or more actuator control commands and/or other information, and the command interface 130 can be configured to communicate one or more actuator control commands along with the associated with or tagged to robot controller 135 and/or other component of the synthetic patient system 1000.

In some further embodiments, data destined for conversion to one or more actuator control commands (the tracked feature points 575 converted to actuator movements) can be modified by the operator 25. For example, in step 440, the data can be parameterized to allow an operator 25 to dampen, attenuate, enhance, or alter in some way the parameters associated with the actuator control commands defining an operator's original facial expressions and head gestures. In some embodiments, the modified data can then be communicated to the robot controller 135, and the control and actuation of the synthetic patient system 1000 can include expression data extracted from the control data 110, 115 with modifications applied by the operator 25.

Figure 5:
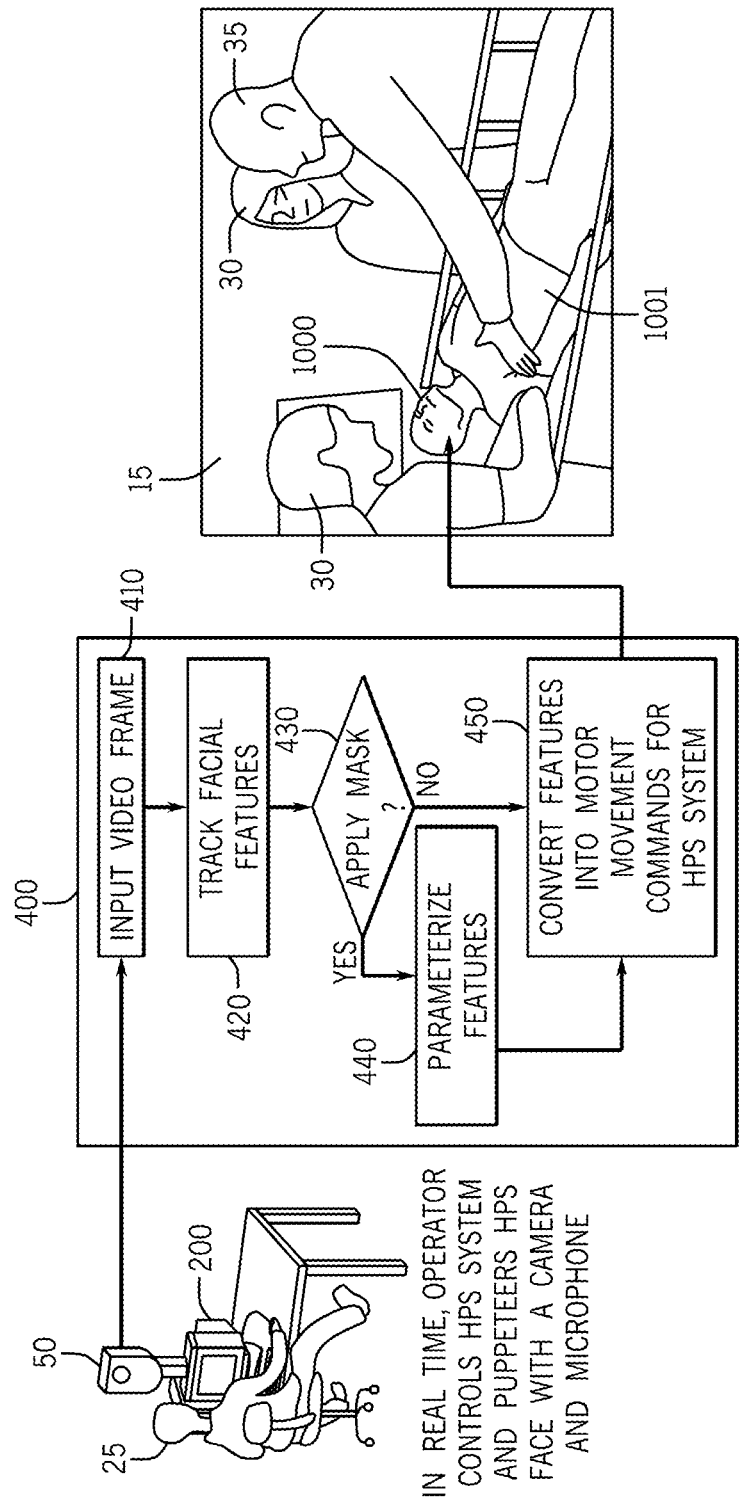
FIG. 5 illustrates an operational sequence flowchart for the synthetic patient system and methods of FIG. 1 in accordance with some embodiments of the invention.

In some embodiments of the invention, control and actuation of the synthetic patient system 1000 using expression data extracted from the control data 110, 115 can occur in an education or training environment. For example, FIG. 5 depicts transfer of data (actuator commands 450) to an education session 15. As illustrated, in some embodiments, the education session 15 can include one or more trainees 30, and one or more doctors, physicians, and/or trainers 35. As shown, in some embodiments, the synthetic patient system 1000 can include a coupled patient abdomen 1001. In some embodiments, the synthetic patient system 1000 can comprise additional anatomical features including, but not limited to, legs, feet, arms, hands, blood, body fluids, and other physiology control systems. Further, as described earlier, in some embodiments, the operator 25 can provide naturalistic facial expressions used in everyday life, as well as specific pathologically-related expressions such as pain and stroke. In this instance, the camera 51 can capture real time control data 115 capturing one or more facial expressions comprising naturalistic facial expressions, or specific pathologically-related expressions. Moreover, in some embodiments of the invention, the operator 25 can modify control and actuation of the synthetic patient system 1000 based on the education session 15. For example, in some embodiments, the operator 25 can modify control and actuation of the synthetic patient system 1000 based on observed actions or behaviors of the one or more trainees 30, and one or more doctors, physicians, and/or trainers 35. In some embodiments, the operator 25 can observe the education session 15 using a sensor 50 coupled to the computer system 200. For example, in some embodiments, sensor 50 can comprise a video camera that is configured to record the education session 15.

FIGS. 7A-7C illustrate examples of transfer of a patient expression (with FIGS. 7A, 7B, and 7C each representing different facial expressions) to an expressive robot with patient expression synthesis in accordance with some embodiments of the invention. For example, FIG. 7A illustrates transfer of a patient expression 27a from a simulated patient or actual patient 27 to an expressive robot 700 with patient expression synthesis 700a in accordance with some embodiments of the invention. FIG. 7B illustrates transfer of a patient expression 27b from a simulated patient or actual patient 27 to an expressive robot 700 with patient expression synthesis 700b in accordance with another embodiment of the invention. Further, FIG. 7C illustrates transfer of a patient expression 27c from a simulated patient or actual patient 27 to an expressive robot 700 with patient expression synthesis 700c in accordance with another embodiment of the invention. In some embodiments, the operator 25 illustrated in FIG. 5 can comprise the simulated patient or actual patient 27. Further, in some embodiments, the synthetic patient system 1000 shown depicted in the education session 15 can comprise the expressive robot 700 configured to be modified by the synthetic patient system and method 10 to comprise the patient expression synthesis 700a, 700b, 700c. Further, in some embodiments, the synthetic patient system 1000 can be configured by the synthetic patient system and method 10 to express other patient expressions based at least in part on control data 110, 115 and optionally, expression parameterization by the operator 25.

In some embodiments, the synthetic patient system 1000 can be configured by the synthetic patient system and method 10 to express any facial expression or affective state, and can also include pathological conditions which affect how the face moves, such as (but not limited to) stroke, dystonia, cerebral palsy, Moebius syndrome, and Parkinson's disease. In any of these examples, or other examples, the reflection and translation of various physical and mental afflictions, facial expressions, gaze, or realistic mouth movements can also be modified and updated substantially in real time by the operator 25.

Figure 8B:
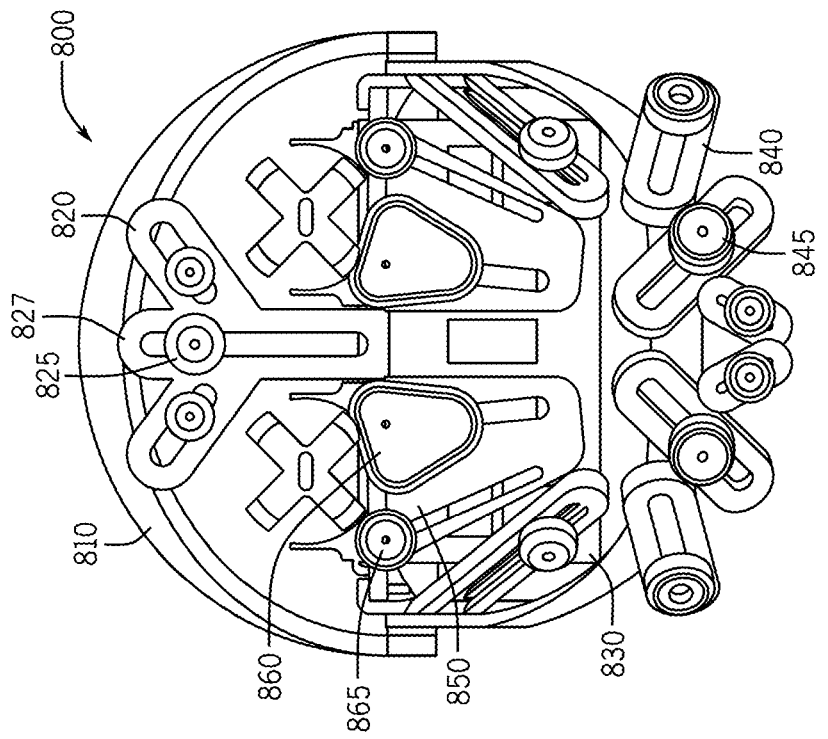
FIG. 8B shows a front view of a robot head assembly in accordance with some embodiments of the invention.
Figure 8A:
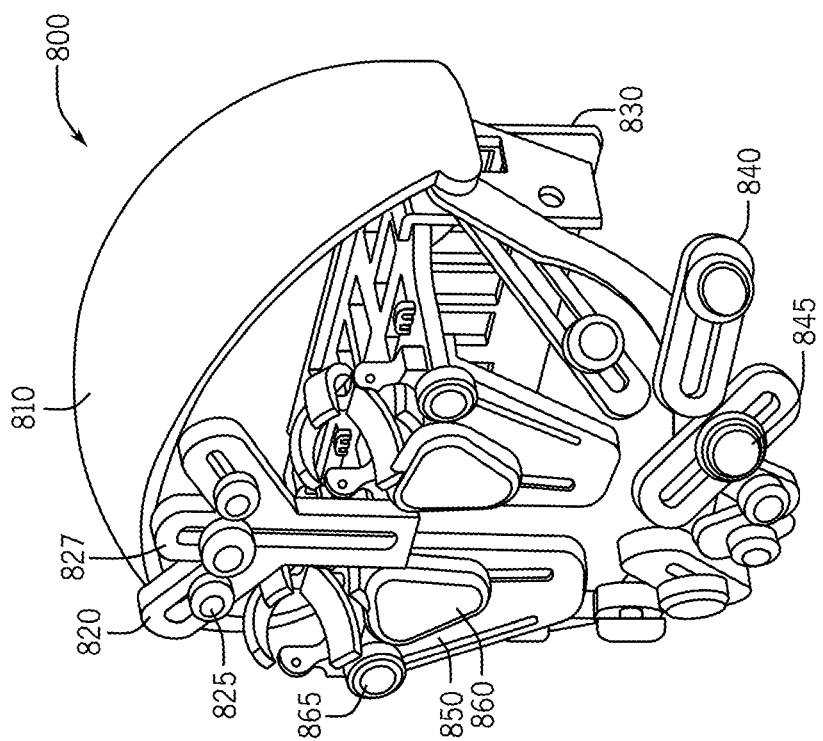
FIG. 8A shows a perspective view of a robot head assembly in accordance with some embodiments of the invention.
Figure 10:
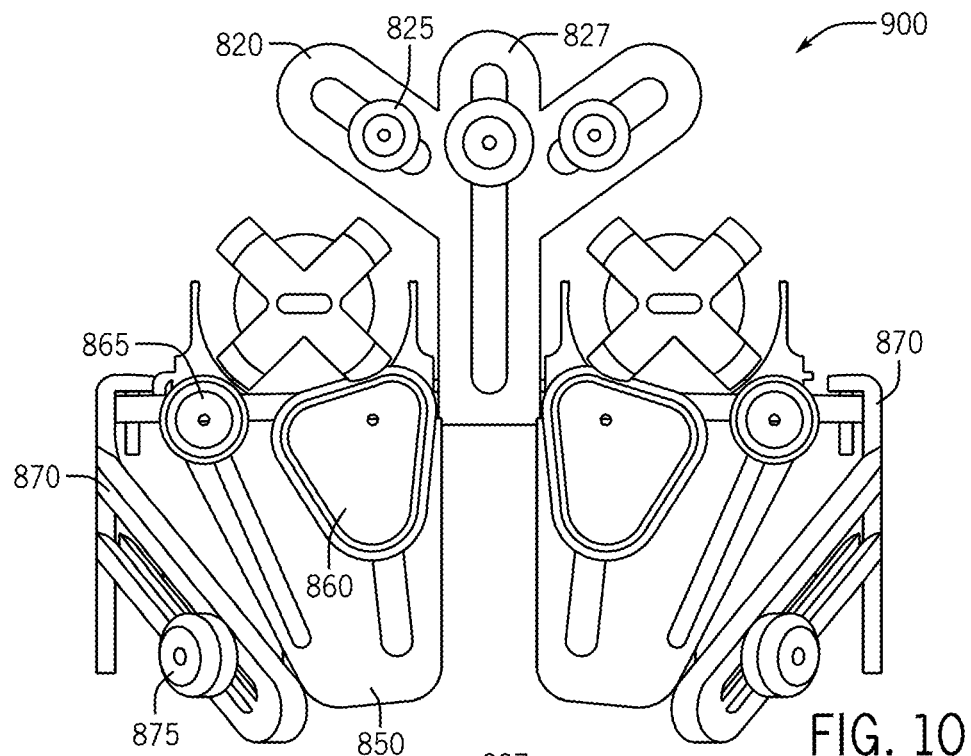
FIG. 10 shows a front view of some portions of a robot head assembly in accordance with some embodiments of the invention.

In some embodiments of the invention, the synthetic patient system 1000 can comprise a robotic head assembly capable of control and actuation by the control system 100. For example, FIG. 8A shows a perspective view of a robot head assembly 800 in accordance with some embodiments of the invention, and FIG. 8B shows a front view of a robot head assembly 800 in accordance with some embodiments of the invention. Further, FIG. 9A shows a bottom view of a robot head assembly 800, and FIG. 9B shows a side view of a robot head assembly 800 in accordance with some embodiments of the invention. In some embodiments, various components of the robot head assembly 800 can be coupled with actuators, motors, gears, power supply and distribution components, and electronics. For instance, in some embodiments, the robot head assembly 800 can include at least one wireless transceiver such as transceiver 140, and the feature detector and action selector 125 (coupled to the server 105 through the transceiver 140). FIG. 10 shows a front view of some portions of a robot head assembly 800 in accordance with some embodiments of the invention to which one or more of these components can be coupled.

In some embodiments, the robot head assembly 800 can comprise an assembly of various support structures, actuator attachment components, movement actuators, and miscellaneous support and attachment components. For example, in some embodiments, as shown at least in FIGS. 8A and 8B, in some embodiments, robot head assembly 800 can comprise a skull cap 810 forming a semi-spherical frame from which various other components of the robot head assembly 800 can be attached, and over which an outer layer of simulated tissue and skin can be coupled. The relative positions of these other components can be seen in FIGS. 9A and 9B, and depict an actuator attachment frame 830 coupled to an eye assembly 820, and a jaw assembly 840 extending away from the actuator attachment frame 830. Further, in some embodiments, the robot head assembly 800 can include one or more structures for cheek support and movement. In some embodiments, the robot head assembly 800 can comprise front cheek portions 850. Further, some embodiments of the invention can include a robot head assembly 800 including front cheek sliders 860 coupled to the front cheek portions 850. Some other embodiments of the invention can comprise a robot head assembly 800 that can comprise additional facial and/or cranial structures to provide support, structure, and definition to the synthetic patient system 1000. In some embodiments, these components can comprise compliant materials to enable deformation, bending, and twisting. For example, in some embodiments, these compliant materials can comprise pourable foam. In other embodiments, pre-shaped cut foam materials can be used in at least some portions of the synthetic patient system 1000.

Figure 11:
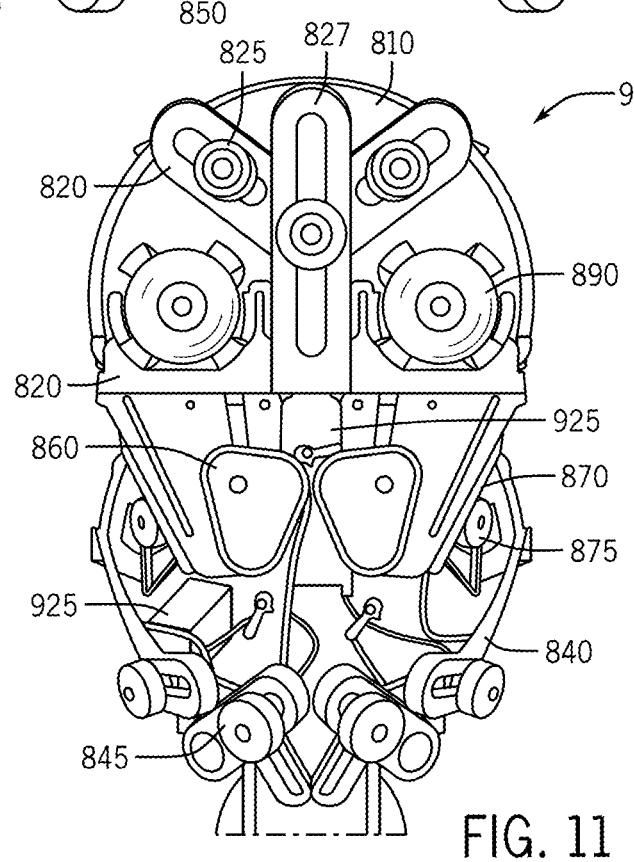
FIG. 11 shows a front view of a robot head assembly in accordance with some embodiments of the invention.
Figure 12:
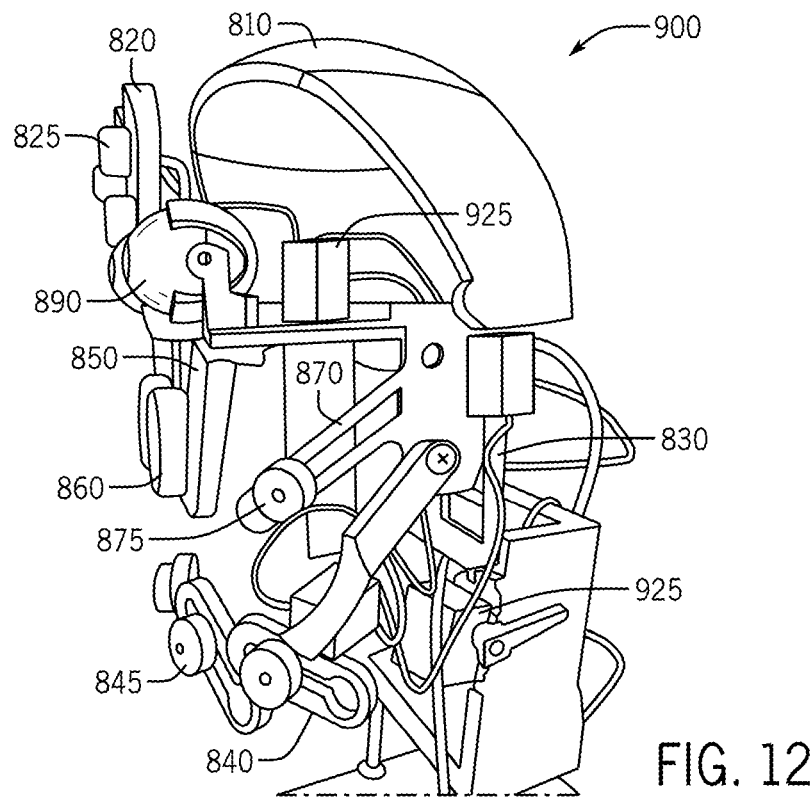
FIG. 12 shows a perspective view of a robot head assembly in accordance with some embodiments of the invention.
Figure 13:
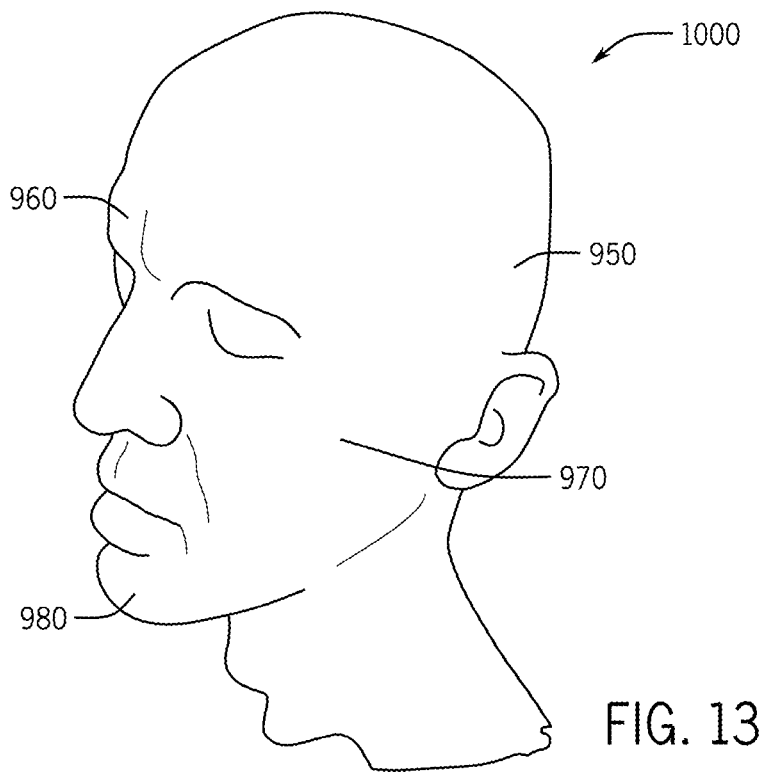
FIG. 13 shows a perspective view of the synthetic patient system in accordance with some embodiments of the invention.

FIG. 11 shows a front view of a robot head assembly 900 in accordance with some embodiments of the invention, and FIG. 12 shows a perspective view of a robot head assembly 900 in accordance with some embodiments of the invention. As illustrated, in some embodiments, the robot head assembly 900 comprises the robot head assembly 800 further integrated with various operating components. In some embodiments, a synthetic outer covering or "skin" is applied to the robot head assembly 900. For example, FIG. 13 shows a perspective view of the synthetic patient system 1000 in accordance with some embodiments of the invention. As shown, in some embodiments, the synthetic patient system 1000 can comprise an outer skin 950 that can enable the synthetic patient system 1000 to comprise a human-like appearance.

In some embodiments, the outer skin 950 can be interchangeable to allow for modifying the race, ethnicity, age, and gender of the synthetic patient system 1000. In some embodiments, the outer skin 950 can comprise a compliant polymer (e.g., an elastomer type material such as a silicone-based polymer). In some embodiments, various portions or regions of the outer skin 950 can be thickened to build a specified appearance into the synthetic patient system 1000. For example, in some embodiments thickness variation can be achieved by adding or removing material to and from the skin in strategic places. For example, a more prominent jaw-line can be replicated by making the skin thicker at the base of the jaw. In some embodiments, paint and/or make-up can be applied to the outer skin 950. Further, in some embodiments, the outer skin 950 can be self-aligning to various attachment portions of the robot head assembly 800, 900. In some embodiments, various conventional attachment/detachment and self-aligning mechanisms can be used including for example, Velcro, releasable adhesive, magnets, hooks, putty, or the like. In some embodiments, magnets can be secured onto portions of the assembly 800, 900 in key locations, such as the base of the neck or the jaw, the back of the head, and corners of the mouth and nose. Corresponding magnets can be embedded within the outer skin 95 to affix the outer skin 950 to the assembly 800, 900 in an appropriate manner.

In some embodiments, the outer skin 950 can be securely attached to the assembly 900 so as not to be prone to loosening or detachment by pushing and pulling of the skin as the synthetic patient system 1000 changes facial expressions, is rotated or pivoted, or is transported. In some embodiments, the control system 100 can comprise a fail-safe to prevent over-stretching of the outer-skin. For example, in some embodiments, the server 105 can include a fail-safe routine to ensure that communication of actuator commands 450 to the command interface 130 and to the robot controller 135 are not likely to over-stretch or tear the outer-skin 950

As shown in FIGS. 11 and 12, one or more actuators 925 can be coupled to portions of the robot head assembly 900. In some embodiments, the actuators can feature very low noise emissions and can be configured and actuated to emit substantially no noise that is audible from outside of the synthetic patient system 1000. In some embodiments, one or more of the actuators 925 can be encased with a variety of conventional noise absorbing and attenuating materials. For example, in some embodiments, foam (e.g., polyurethane foam) can be used to dampen vibrations and reduce noise emissions.

As recited earlier, in some embodiments, the synthetic patient system and method 10 can enable the facial expression data extracted from control data 110, 115 to be communicated to the robot controller 135 to enable control and actuation of the synthetic patient system 1000. Consequently, in some embodiments, control and actuation of various actuators in the synthetic patient system 1000 can enable animated movement of at least a portion of the robot head assembly 800, 900 within the synthetic patient system 1000. In some embodiments of the invention, the robot head assembly 800, 900 can comprise one or more components and/or assemblies for translating and/or enabling movement within the robot head assembly 800, 900. For example, in some embodiments, the robot head assembly 800, 900 can comprise one or more moveable components comprising sliders that are configured to be coupled to one or more portions of the robot head assembly 800, 900, and powered or moveable by actuators (at least some of which are attached to the actuator attachment frame 830). In some embodiments, the sliders can be actuated by one or more actuators to enable movement of at least a portion of the robot head assembly 800, 900. In some embodiments, the addition of moveable sliders, positioned beneath the outer skin 950, and coupled to facial and/or cranial structures can provide the ability to provide a combination of animated support, structure, and definition to enable the synthetic patient system 1000 to provide facial expression changes and gestures. For example, some embodiments of the invention comprise frontal sliders 825 coupled to the eye assembly 820. In some embodiments, the frontal sliders 825 can be actuated by one or more actuators 925, and can move within tracks 827. Consequently, in some embodiments, one or more of the frontal sliders 825 can be actuated by one or more actuators 925 to enable movement of at least a portion of the brow region 960 (shown in FIG. 13) as the frontal sliders 825 move within the tracks 827. Accordingly, in some embodiments, actuation of at least one of the actuators 925 can translate movement to the outer skin 950.

In some further embodiments, at least one eye 890 can be coupled to the eye assembly 820. In some embodiments, one or more actuators 925 can be coupled to the eye assembly 820 and can coupled to the at least one eye 890 to enable movement of the at least one eye 890. In some embodiments, at least some portion of the at least one eye 890 can protrude through the outer skin 950 and/or through a hole or gap in the outer skin 950 of the synthetic patient system 1000 shown in FIG. 13.

In some further embodiments, one or more jaw sliders 845 can be slideably coupled to various locations on the jaw assembly 840. Accordingly, in some embodiments, one or more jaw sliders 845 can be actuated by one or more actuators 925 to enable movement of at least a portion of jaw region 980 (shown in FIG. 13). In some other embodiments, the robot head assembly 800, 900 can comprise one or more sliders coupled to the front cheek portions 850 including front cheek sliders 860, and optional secondary cheek sliders 865. Further, some embodiments of the invention can include a side cheek portion 870 and side cheek sliders 875. Accordingly, in some embodiments, at least one of the sliders 860, 865, 875 can be actuated by one or more actuators 925 to enable movement of at least a portion of cheek region 970 (shown in FIG. 13). In some further embodiments, other conventional movement translation components can be utilized in place of and/or in addition to the sliders 825, 845, 860, 865, 875. For example, in some embodiments, a slider can comprise a conventional washer that is configured to slide in rails to create a moveable actuator. In some further embodiments, the sliders 825, 845, 860, 865, 875 can comprise a expandable or moveable elastic element (such as an elastic band coupled to a fixed post at one end, or at both ends). In some further embodiments, the sliders 825, 845, 860, 865, 875 can comprise a gear element moveably coupled to a linear or rotary gear. In some other embodiments, at least a portion of the robot head assembly 800, 900 can be moved using other conventional movement assemblies comprising, for example, conventional pulleys, wires, and pneumatic actuators. In other embodiments, hydraulic and/or electronic actuators can be used. In some embodiments, any of the sliders 825, 845, 860, 865, 875 can comprise these movement assemblies. Further, in any of the embodiments described herein, movement actuators and assemblies, including sliders 825, 845, 860, 865, 875 are configured to operate with reduced noise. Therefore, in some embodiments, actuation of the sliders 825, 845, 860, 865, 875 is not audible outside of the synthetic patient system 1000.

In some embodiments of the invention, the synthetic patient system 1000 can comprise additional sensors and actuators that can be configured to increase the life-like appearance and motion of the synthetic patient system 1000. For example, in some embodiments, the synthetic patient system 1000 can include additional actuators such as a sound generator (including, for example, a loud-speaker shown as 927 in FIG. 1) to enable the synthetic patient system 1000 to emit sound, play recorder speech, or produce synthetic speech.

Some embodiments of the invention also relate to a device or an apparatus for performing the various processes and methods as described herein. In some embodiments, the apparatus can be specially constructed for the required purpose, such as a special purpose computer. In some embodiments, when defined as a special purpose computer, the computer can also perform other processing, program execution or routines that are not part of the special purpose, while still being capable of operating for the special purpose. Alternatively, in some other embodiments, the operations can be processed by a general purpose computer selectively activated or configured by one or more computer programs stored in the computer memory, cache, or obtained over a network. Some embodiments include instances when data are obtained over a network, and where the data can be processed by other computers on the network, e.g. a cloud of computing resources.

With the above embodiments in mind, it should be understood that some embodiments of the invention can employ various computer-implemented operations involving data stored in computer systems (such as the computer system 200 shown in FIG. 3). Moreover, in some embodiments, the above-described databases and models processed by the synthetic patient system and method 10 under direction of the control system 100 can store analytical models and other data on computer-readable storage media (including for example the mass storage device 207, as well as other conventional storage device coupled to the computer system 200). In addition, in some embodiments, the above-described applications of the monitoring system can be stored on computer-readable storage media. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

In some embodiments, the invention can also be embodied as computer readable code on a computer readable medium. Some embodiments include a computer readable medium that can be any data storage device that can store data, which can thereafter be read by a computer system (e.g., such as mass storage device 207 shown in FIG. 3). Examples of the computer readable medium can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer system 200 and/or processor 202.

In some embodiments, the computer readable medium can also be distributed over a conventional computer network via the network interface so that the computer readable code can be stored and executed in a distributed fashion. For example, in some embodiments, one or more components of the computer system 200 can be tethered to send and/or receive data through a local area network ("LAN"). In some further embodiments, one or more components of the computer system 200 can be tethered to send or receive data through an internet (e.g., a wireless internet). In some embodiments, at least one software application running on at least one processor 202 can be configured to be coupled for communication over a network.

In some embodiments, one or more components of the network can include one or more resources for data storage, including any other form of computer readable media beyond the media for storing information and including any form of computer readable media for communicating information from one electronic device to another electronic device This can include the mass storage device 207, or another conventional storage device coupled to the computer system 200. Also, in some embodiments, the network can include wide area networks ("WAN"), direct connections (e.g., through a universal serial bus port) or other forms of computer-readable media, or any combination thereof. Also, various other forms of computer-readable media can transmit or carry instructions to a computer, including a router, private or public network, or other transmission device or channel, both wired and wireless. In some embodiments, the software modules can be configured to send and receive data from a database (e.g., from a computer readable medium including data sources and data storage that can comprise a database), and data can be received by the software modules from at least one other source. In some embodiments, at least one of the software modules can be configured within the system to output data to a user via at least one digital display (e.g., to a computer comprising a digital display).

In some embodiments, one or more components of the computer system 200 shown in FIG. 3 can include a number of coupled client devices that can be personal computers including for example desktop computers, laptop computers, digital assistants, personal digital assistants, cellular phones, mobile phones, smart phones, pagers, digital tablets, internet appliances, and other processor-based devices. In general, a user device can be any type of external or internal devices such as a mouse, a CD-ROM, DVD, a keyboard, a display, or other input or output devices. In some embodiments, the communication device 225 can comprise the above mentioned client devices.

Any of the operations described herein that form part of the invention are useful machine operations. The invention also relates to a device or an apparatus for performing these operations. The embodiments of the present invention can be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A robotic patient system comprising:
    a computer system including at least one processor and at least one coupled sensor;
    a control system configured and arranged to generate robot control commands and a synthetic patient robot configured and arranged to be responsive to the robot control commands;
    the control system configured to be coupled to at least one source of control data,
    the control system comprising:
        a feature tracker;
        a command interface;
        actuator command processor configured to extract one or more facial features or expressions from control data provided by the at least one source of control data;
        a server coupled to the command interface and the feature tracker; and
    wherein the synthetic patient robot comprises:
        a robotic head assembly, a robot controller, and at least one actuator;
        the robot controller configured to be coupled to the command interface using a link; and
        wherein at least a portion of the synthetic patient robot is configured and arranged to respond to actuator control commands processed by the actuator command processor based at least in part on one or more facial features or expressions extracted from the feature tracker.

2. The system of claim 1, wherein the server is coupled to the the actuator command processor.

3. The system of claim 2, wherein the at least one actuator is configured to receive the actuator control commands from the actuator command processor via the command interface under control of the server.

4. The system of claim 1, wherein the control data comprises pre-recorded data.

5. The system of claim 1, wherein the control data comprises substantially real time collected information; and
    wherein the synthetic patient robot is configured to respond to the actuator control commands based at least in part on the substantially real time collected information.

6. The system of claim 1, wherein the control data includes information derived from at least one of a patient image, an actor, an operator, and a patient medical record.

7. The system of claim 1, wherein at least a portion of the control data is derived from the at least one sensor.

8. The system of claim 7, wherein the at least one sensor comprises a camera and at least a portion of the control data is derived from at least one image.

9. The system of claim 1, wherein at least a portion of the control data is received from an operator.

10. The system of claim 1, wherein the synthetic patient robot comprises a wireless interface and the link comprises the wireless interface wirelessly coupled to the control system.

11. The system of claim 1, wherein the link comprises a wired interface.

12. The system of claim 1, wherein the robotic head assembly includes at least one slider configured to be actuated by the at least one actuator.

13. The system of claim 12, wherein actuation of the at least one slider is not audible outside of the synthetic patient robot.

14. The system of claim 1, wherein the robotic head assembly further comprises an outer skin; and
    wherein at least a portion of the outer skin can be moved by the at least one actuator.

15. The system of claim 14, wherein movement of at least a portion of the outer skin induces or changes a perceived expression from the synthetic patient robot.

16. The system of claim 14, wherein the outer skin is interchangeable and configurable to modify a perception of at least one of race, ethnicity, age, and gender.

17. The system of claim 1, wherein the synthetic patient robot includes a sound generator.

18. The system of claim 17, wherein the sound generator is configured and arranged to emit sound based at least in part on the control data or the at least one actuator.

19. The system of claim 18, wherein the at least one actuator comprises at least one sensor responsive to external stimuli.

20. The system of claim 19, wherein at least a portion of the robotic head assembly is configured and arranged to be independently actuated to provide a perceivable expression and substantially simultaneously emit sound following a detected response from an external stimuli.

21. A computer-implemented method of providing a robotic synthetic patient, comprising:
   providing a computer system including at least one processor and at least one coupled sensor;
   providing a synthetic patient robot, the robot comprising an actuator command processor, a robotic head assembly and at least one actuator; and
   receiving control data from at least one control data source;
   providing a control system comprising:
      a feature tracker;
      a command interface;
      the actuator command processor;
      a server coupled to the command interface; and
   using the at least one processor, configuring the control system to receive the control data;
   using the at least one processor and the feature tracker, extracting at least one feature from the control data and converting to at least one actuator command; and
      wherein at least a portion of the synthetic patient robot is configured and arranged to respond to the at least one actuator command.

22. The computer-implemented method of claim 21, wherein the control system further comprises an actuator command processor; and
   wherein the server is coupled to the feature tracker and the actuator command processor; and
   wherein the at least one feature is processed from the control data by the feature tracker and the actuator command processor to produce the least one actuator command.

23. The computer-implemented method of claim 21, wherein the control data comprises information derived from at least one patient image.

24. The computer-implemented method of claim 23, wherein the at least one patient image is pre-recorded.

25. The computer-implemented method of claim 23, wherein the control data comprises substantially real time collected information; and
   wherein the control data is received and the synthetic robot responds to the least one actuator command at least in part based on the control data substantially in real time.

26. The computer-implemented method of claim 21, wherein the at least one actuator command can be modified based at least in part on input from an operator.

27. The computer-implemented method of claim 21, wherein the control data is derived from at least a partial portion of the face of the operator.

28. The computer-implemented method of claim 21, wherein the control data is received from the operator.

29. The computer-implemented method of claim 21, wherein the control data is received from the synthetic patient robot.

30. The computer-implemented method of claim 29, wherein the synthetic patient robot is configured and arranged to operate substantially autonomously.

31. A synthetic patient robot comprising:
   a synthetic patient robot including a robotic head assembly and at least one actuator;
   a computer system including at least one processor;
   a non-transitory computer-readable storage medium in data communication with the at least one processor;
   a control system configured to be coupled to at least one source of control data, the control system including a feature tracker;
   wherein at least a portion of the synthetic patient robot is configured and arranged to be operated substantially autonomously by the control system based at least in part on at least one feature extracted by the feature tracker from the control data using the at least one processor.

32. The robot of claim 31, wherein the at least one source of control data is the non-transitory computer-readable storage medium.

33. The robot of claim 31, wherein the control data is configured to be received by the synthetic patient robot prior to operation of the synthetic patient robot.

34. The robot of claim 31, wherein the control data is received by the synthetic patient robot substantially in real time during operation of the synthetic patient robot.

35. The robot of claim 31, wherein the control data comprises information derived from at least one of a patient image, an actor, an operator, and a patient medical record.

* * * * *